United States Patent
Maruyama

(10) Patent No.: US 11,021,430 B2
(45) Date of Patent: Jun. 1, 2021

(54) OXA ACID COMPOUND

(71) Applicant: Moresco Corporation, Kobe (JP)

(72) Inventor: Shingo Maruyama, Kobe (JP)

(73) Assignee: Moresco Corporation, Kobe (JP)

( * ) Notice: Subject to any disclaimer, the term of this patent is extended or adjusted under 35 U.S.C. 154(b) by 0 days.

(21) Appl. No.: 16/089,283

(22) PCT Filed: Mar. 1, 2017

(86) PCT No.: PCT/JP2017/008053
§ 371 (c)(1),
(2) Date: Sep. 27, 2018

(87) PCT Pub. No.: WO2017/175522
PCT Pub. Date: Oct. 12, 2017

(65) Prior Publication Data
US 2019/0106373 A1  Apr. 11, 2019

(30) Foreign Application Priority Data
Apr. 5, 2016 (JP) .............................. JP2016-076176

(51) Int. Cl.
*C07C 59/125* (2006.01)
*C07B 61/00* (2006.01)

(52) U.S. Cl.
CPC ............ *C07C 59/125* (2013.01); *C07B 61/00* (2013.01)

(58) Field of Classification Search
USPC ........................................................ 562/587
See application file for complete search history.

(56) References Cited

U.S. PATENT DOCUMENTS

| | | | |
|---|---|---|---|
| 4,302,394 A | 11/1981 | Dennis | |
| 4,559,337 A | 12/1985 | Mueller | |
| 4,960,540 A | 10/1990 | Friel, Jr. et al. | |
| 5,082,967 A | 1/1992 | Heuckeroth et al. | |
| 5,747,537 A | 5/1998 | Gordon et al. | |
| 5,859,052 A | 1/1999 | Nugent et al. | |
| 5,871,954 A | 2/1999 | Heuckeroth et al. | |
| 2004/0067202 A1 | 4/2004 | Looker et al. | |
| 2006/0018874 A1 | 1/2006 | Radhakrishnan et al. | |
| 2008/0318070 A1 | 12/2008 | Hirao et al. | |
| 2012/0028888 A1* | 2/2012 | Janz ................. | A61P 35/04 514/3.8 |
| 2012/0123168 A1 | 5/2012 | Bhavaraju | |
| 2016/0009669 A1 | 1/2016 | Koga et al. | |

FOREIGN PATENT DOCUMENTS

| | | | |
|---|---|---|---|
| GB | 1165199 A | | 9/1969 |
| JP | S55141480 A | | 11/1980 |
| JP | S61200975 A | | 9/1986 |
| JP | 02001425 | | 1/1990 |
| JP | H05271181 A | | 10/1993 |
| JP | H6346259 A | | 12/1994 |
| JP | H0859545 A | | 3/1996 |
| JP | H11246473 A | | 9/1999 |
| JP | 2000511900 A | | 9/2000 |
| JP | 2003513884 A | | 4/2003 |
| JP | 2004509159 A | | 3/2004 |
| JP | 2008506782 A | | 3/2008 |
| JP | 2008225166 A | | 9/2008 |
| JP | 2012106948 A | | 6/2012 |
| JP | 2014507527 A | | 3/2014 |
| JP | 2015224283 A | | 12/2015 |
| WO | WO 92/03412 | * | 12/1992 |
| WO | WO-9746231 A1 | | 12/1997 |
| WO | 1998017315 A2 | | 4/1998 |
| WO | WO-9838988 | * | 9/1998 |
| WO | WO-0067801 A2 | | 11/2000 |
| WO | WO-2011148520 A1 | | 12/2011 |
| WO | WO-2014087646 A1 | | 6/2014 |

OTHER PUBLICATIONS

Otte et al. European Journal of Organic Chemistry (2013), 11, 2130-2139.*
International Search Report from PCT Application No. PCT/JP2017/008053 dated May 9, 2017 (3 pages).
International Preliminary Report of Patentability from PCT Application No. PCT/JP2017/008053 dated Oct. 9, 2018 (7 pages).
Extended European Search Report from corresponding European Application No. 17778901.3 dated Oct. 24, 2019.
Taubitz, Jörg and Lüning, Ulrich, "On the Importance of the Nature of Hydrogen Bond Donors in Multiple Hydrogen Bond Systems," Eur. J. Org. Chem, 5922-5927 (2008).
Adam, W. et al., "α Hydroxylation of Carboxylic Acids with Molecular Oxygen Catalyzed by the α Oxidase of Peas (*Pisum sativum*): A Novel Biocatalytic Synthesis of Enantiomerically Pure (R)-2-Hydroxy Acids," J. Am. Chem. Soc., 120: 11044-11048 (1998).
Office Action from corresponding European Application No. 17778901.3 dated Mar. 11, 2021.

* cited by examiner

*Primary Examiner* — Ana Z Muresan
(74) *Attorney, Agent, or Firm* — Harness Dickey & Pierce P.L.C.

(57) ABSTRACT

Provided herein are various oxa acids having respective molecular weights and hydrophile-lipophile balances both different from each other. A compound having a structure represented by the following formula (1)

[Chem. 1]

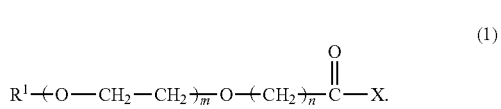

(1)

$$R^1\!-\!(O\!-\!CH_2\!-\!CH_2)_{\overline{m}}\!-\!O\!-\!(CH_2)_{\overline{n}}\!-\!\overset{O}{\overset{\|}{C}}\!-\!X.$$

1 Claim, 3 Drawing Sheets

[Example 1]

[Example 4]

[Example 9]

[Example 11]

[Example 12]

[Example 13]

OXA ACID COMPOUND

PRIORITY STATEMENT

This application is a national stage application under 35 U.S.C. § 371 of PCT International Application No. PCT/JP2017/008053, which has an International filing date of 1 Mar. 2017 and claims priority to Japanese Patent Application No. JP 2016-076176 which has a filing date of 5 Apr. 2016. The contents of each application recited above are incorporated herein by reference in their entirety.

TECHNICAL FIELD

The present invention relates to an oxa acid compound.

BACKGROUND ART

Tokuhyo No. 2000-511900 (Patent Literature 1) discloses using, as an active main component for treating a skin symptom, an oxa acid containing a carbonyl group having an oxygen atom at the beta position. Tokuhyo No. 2003-513884 (Patent Literature 2) discloses covalently bonding (i) an oxa acid containing a carbonyl group having an oxygen atom at the beta position with (ii) a pharmaceutical drug to produce a prodrug.

CITATION LIST

Patent Literature

[Patent Literature 1]
Japanese Translation of PCT International Application, Tokuhyo, No. 2000-511900 (Publication Date: Sep. 12, 2000)
[Patent Literature 2]
Japanese Translation of PCT International Application, Tokuhyo, No. 2003-513884 (Publication Date: Apr. 15, 2003)

SUMMARY OF INVENTION

Technical Problem

Recent years have seen an increase in the importance of an oxa acid compound (which is an ether-containing fatty acid-based compound) in the fields of drug delivery systems (DDSs) and cosmetics. Example applications in the field of DDSs include an application as an absorption promotor for use after oral administration of a pharmaceutical drug, an application as a promotor of percutaneous absorption of an effective substance, and an application for producing a prodrug of a pharmacologically active substance. Example applications in the field of cosmetics include an application as an absorption promotor for use after oral administration of a health promoting substance (so-called supplement) and an application as a promotor of percutaneous absorption of a cosmetic product.

Providing various oxa acids having different molecular weights and different hydrophile-lipophile balances will be helpful in the polarity control for the dosage form design in the fields of DDSs and cosmetics.

The present invention has been accomplished in view of the above issue. It is an object of the present invention to provide various oxa acids having respective molecular weights and hydrophile-lipophile balances both different from each other.

Solution to Problem

In order to attain the above object, a compound in accordance with an embodiment of the present invention has a structure represented by a formula (1) below:

[Chem. 1]

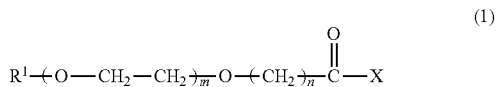
(1)

where $R^1$ represents a linear or branched hydrocarbon group having 1 to 36 carbon atoms, one or more but not all carbon atoms of which hydrocarbon group have each optionally been substituted by an oxygen atom, a nitrogen atom, or a sulfur atom; m represents an integer of 0 to 35; n represents an integer of 2 to 5; and —C(=O)—X represents a functional group capable of chemical reaction, or
a formula (2) below:

[Chem. 2]

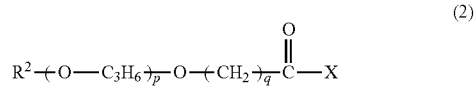
(2)

where $R^2$ represents a linear or branched hydrocarbon group having 1 to 36 carbon atoms, one or more but not all carbon atoms of which hydrocarbon group have each optionally been substituted by an oxygen atom, a nitrogen atom, or a sulfur atom; p represents an integer of 0 to 30; q represents an integer of 2 to 5; and —C(=O)—X represents a functional group capable of chemical reaction.

Advantageous Effects of Invention

An embodiment of the present invention provides various oxa acids having respective molecular weights and hydrophile-lipophile balances both different from each other.

DESCRIPTION OF EMBODIMENTS

Figure 1:
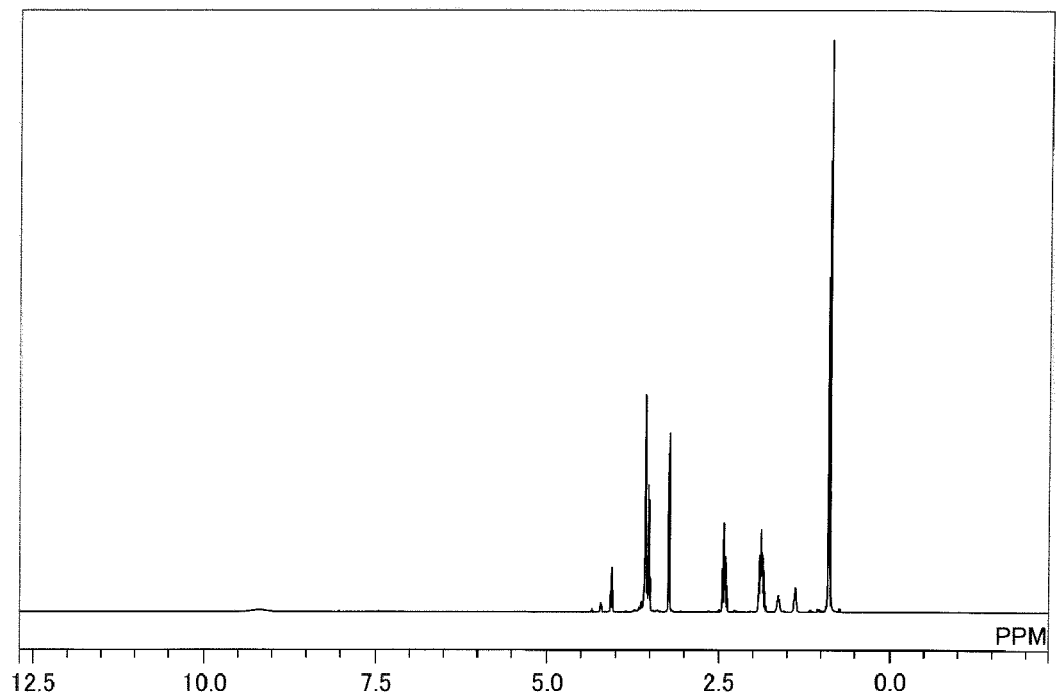
FIG. 1 is a $^1$H-NMR chart for a compound produced in Example 1 of the present invention.

The following will describe an embodiment of the present invention in detail. Note, however, that the present invention is not limited to that embodiment. The present invention can be carried out in specific forms into which various modifications are incorporated within the scope set forth herein. All of the academic documents and patent literatures listed herein are incorporated by reference herein. Unless otherwise specified herein, "A to B" which indicates a numerical range means "not less than A and not more than B".

[Compound in accordance with an embodiment of the present invention]

A compound in accordance with an embodiment of the present invention has a structure represented by the following formula (1):

[Chem. 3]

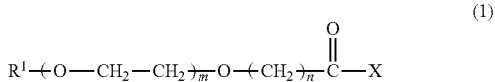

(1)

where $R^1$ represents a linear or branched hydrocarbon group having 1 to 36 carbon atoms, one or more but not all carbon atoms of which hydrocarbon group have each optionally been substituted by an oxygen atom, a nitrogen atom, or a sulfur atom; m represents an integer of 0 to 35; n represents an integer of 2 to 5; and —C(=O)—X represents a functional group capable of chemical reaction, or the following formula (2):

[Chem. 4]

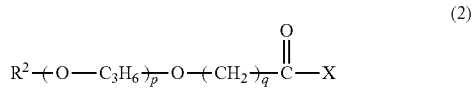

(2)

where $R^2$ represents a linear or branched hydrocarbon group having 1 to 36 carbon atoms, one or more but not all carbon atoms of which hydrocarbon group have each optionally been substituted by an oxygen atom, a nitrogen atom, or a sulfur atom; p represents an integer of 0 to 30; q represents an integer of 2 to 5; and —C(=O)—X represents a functional group capable of chemical reaction.

In the formula (1) above, $R^1$ simply needs to have 1 to 36 carbon atoms, but preferably has 2 to 36 carbon atoms, more preferably 4 to 36 carbon atoms, even more preferably 6 to 36 carbon atoms, particularly preferably 8 to 36 carbon atoms, most preferably 9 to 36 carbon atoms. Further, $R^1$ may be linear or branched.

$R^1$ may be a hydrocarbon group, or may be a hydrocarbon group one or more but not all carbon atoms of which hydrocarbon group may each have been substituted by an oxygen atom, a nitrogen atom, or a sulfur atom.

$R^1$ may be saturated or unsaturated. $R^1$ is, however, preferably a saturated hydrocarbon group or a saturated hydrocarbon group one or more but not all carbon atoms of which saturated hydrocarbon group have each been substituted by an oxygen atom, a nitrogen atom, or a sulfur atom.

m simply needs to be an integer of 0 to 35, but is preferably an integer of 0 to 20. n simply needs to be an integer of 2 to 5, but is preferably an integer of 3 or 4, more preferably 3.

Examples of preferable combinations of $R^1$, m, and n in the formula (1) above include the following combinations (A) to (E):

(A) $R^1$ represents a linear or branched hydrocarbon group having 2 to 36 carbon atoms, one or more but not all carbon atoms of which hydrocarbon group have each optionally been substituted by an oxygen atom, a nitrogen atom, or a sulfur atom; m represents an integer of 0 to 20; and n represents 3 or 4

(B) $R^1$ represents a linear or branched hydrocarbon group having 4 to 36 carbon atoms, one or more but not all carbon atoms of which hydrocarbon group have each optionally been substituted by an oxygen atom, a nitrogen atom, or a sulfur atom; m represents an integer of 0 to 20; and n represents 3 or 4

(C) $R^1$ represents a linear or branched hydrocarbon group having 6 to 36 carbon atoms, one or more but not all carbon atoms of which hydrocarbon group have each optionally been substituted by an oxygen atom, a nitrogen atom, or a sulfur atom; m represents an integer of 0 to 20; and n represents 3 or 4

(D) $R^1$ represents a linear or branched hydrocarbon group having 8 to 36 carbon atoms, one or more but not all carbon atoms of which hydrocarbon group have each optionally been substituted by an oxygen atom, a nitrogen atom, or a sulfur atom; m represents an integer of 0 to 20; and n represents 3 or 4

(E) $R^1$ represents a linear or branched hydrocarbon group having 9 to 36 carbon atoms, one or more but not all carbon atoms of which hydrocarbon group have each optionally been substituted by an oxygen atom, a nitrogen atom, or a sulfur atom; m represents an integer of 0 to 20; and n represents 3 or 4

In the formula (2), the divalent hydrocarbon group "—$C_3H_6$—" simply needs to be a saturated hydrocarbon group having 3 carbon atoms, and may be linear or branched. Examples of the divalent hydrocarbon group "—$C_3H_6$—" in the formula (2) include —$CH_2$—$CH_2$—$CH_2$—, —$CH(CH_3)$—$CH_2$—, —$CH_2$—$CH(CH_3)$—, —$CH(CH_2$—$CH_3)$—, and —$C(CH_3)_2$—.

In the formula (2) above, $R^2$ simply needs to have 1 to 36 carbon atoms, but preferably has 2 to 36 carbon atoms, more preferably 4 to 36 carbon atoms, even more preferably 6 to 36 carbon atoms, particularly preferably 8 to 36 carbon atoms, most preferably 9 to 36 carbon atoms. Further, $R^2$ may be linear or branched.

$R^2$ may be a hydrocarbon group, or may be a hydrocarbon group one or more but not all carbon atoms of which hydrocarbon group may each have been substituted by an oxygen atom, a nitrogen atom, or a sulfur atom.

$R^2$ may be saturated or unsaturated. $R^2$ is, however, preferably a saturated hydrocarbon group or a saturated hydrocarbon group one or more but not all carbon atoms of which saturated hydrocarbon group have each been substituted by an oxygen atom, a nitrogen atom, or a sulfur atom.

p simply needs to be an integer of 0 to 30, but is preferably an integer of 0 to 20. q simply needs to be an integer of 2 to 5, but is preferably an integer of 3 or 4, more preferably 3.

Examples of preferable combinations of $R^2$, p, and q in the formula (2) above include the following combinations (F) to (J):

(F) $R^2$ represents a linear or branched hydrocarbon group having 2 to 36 carbon atoms, one or more but not all carbon atoms of which hydrocarbon group have each optionally been substituted by an oxygen atom, a nitrogen atom, or a sulfur atom; p represents an integer of 0 to 20; and q represents 3 or 4

(G) $R^2$ represents a linear or branched hydrocarbon group having 4 to 36 carbon atoms, one or more but not all carbon atoms of which hydrocarbon group have each optionally been substituted by an oxygen atom, a nitrogen atom, or a sulfur atom; p represents an integer of 0 to 20; and q represents 3 or 4

(H) $R^2$ represents a linear or branched hydrocarbon group having 6 to 36 carbon atoms, one or more but not all carbon atoms of which hydrocarbon group have each optionally been substituted by an oxygen atom, a nitrogen atom, or a sulfur atom; p represents an integer of 0 to 20; and q represents 3 or 4

(I) $R^2$ represents a linear or branched hydrocarbon group having 8 to 36 carbon atoms, one or more but not all carbon atoms of which hydrocarbon group have each optionally been substituted by an oxygen atom, a nitrogen atom, or a sulfur atom; p represents an integer of 0 to 20; and q represents 3 or 4

(J) $R^2$ represents a linear or branched hydrocarbon group having 9 to 36 carbon atoms, one or more but not all carbon atoms of which hydrocarbon group have each optionally been substituted by an oxygen atom, a nitrogen atom, or a sulfur atom; p represents an integer of 0 to 20; and q represents 3 or 4

In the formulae (1) and (2), —C(=O)—X simply needs to be a functional group capable of chemical reaction. —C(=O)—X as a functional group capable of chemical reaction will react with a functional group present in, for example, a pharmaceutical drug, a physiologically active substance, or a biofunctional molecule. This allows a compound in accordance with an embodiment of the present invention to be used suitably in an application as a promotor of absorption of a pharmaceutical drug or an application for producing a prodrug of a pharmacologically active substance.

More specifically, —C(=O)—X is preferably selected from the group consisting of an active ester group, an aldehyde group, a carboxymaleimide group, a carboxy group, a carbamoyl group, a carbazoyl group, and a haloformyl group.

More specifically, the active ester is, for example, an active ester in which X represents a succinimidyloxy group, a 4-nitrophenoxy group, a phthalimidyloxy group, a 1-imidazolyl group, a pentafluorophenoxy group, a benzotriazole-1-yloxy group, or a 7-azabenzotriazole-1-yloxy group. The haloformyl group is, for example, a fluoroformyl group, a chloroformyl group, a bromoformyl group, or an iodoformyl group.

X in the formulae (1) and (2) is, in particular, preferably a group represented by one of the following formulae (a) to (k):

[Chem. 5]

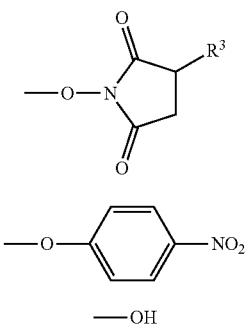
(a)

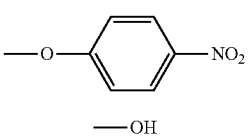
(b)

—OH (c)

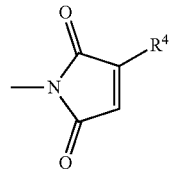
(d)

—$NH_2$ (e)

—$NHNH_2$ (f)

—H (g)

—F (h)

—Cl (i)

—Br (j)

—I (k)

In the formula (a), $R^3$ represents a hydrogen atom or a sulfo group. The sulfo group is, for example, sodium sulphonate or potassium sulphonate. $R^3$ is preferably a hydrogen atom. In the formula (d), $R^4$ is a hydrogen atom or a linear or branched hydrocarbon group having 1 to 5 carbon atoms.

Specific examples of a compound in accordance with an embodiment of the present invention include compounds having respective structures represented by the following formula (3) to (15):

[Chem. 6]

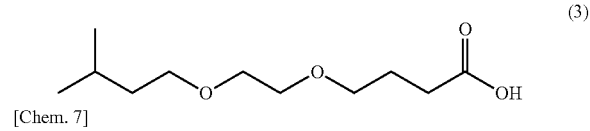
(3)

[Chem. 7]

(4)

[Chem. 8]

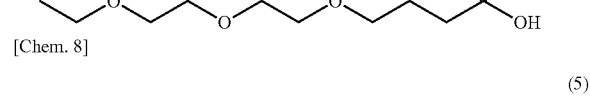
(5)

[Chem. 9]

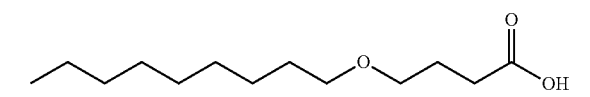
(6)

[Chem. 10]

(7)

-continued

[Chem. 11]

(8)

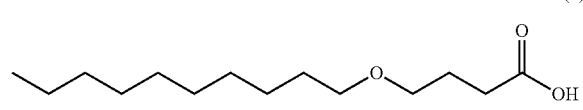

[Chem. 12]

(9)

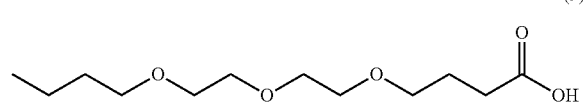

[Chem. 13]

(10)

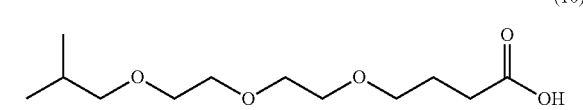

[Chem. 14]

(11)

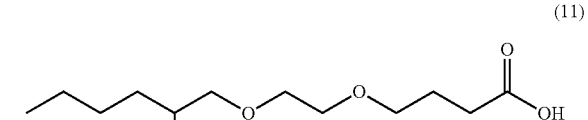

[Chem. 15]

(12)

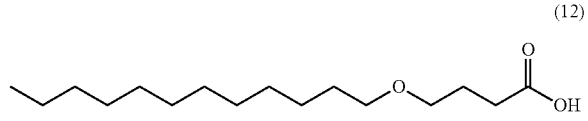

[Chem. 16]

(13)

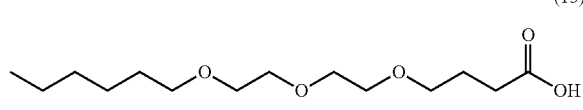

[Chem. 17]

(14)

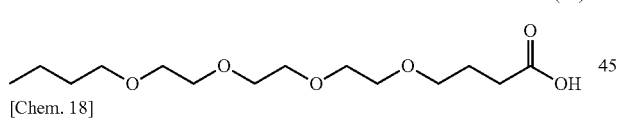

[Chem. 18]

(15)

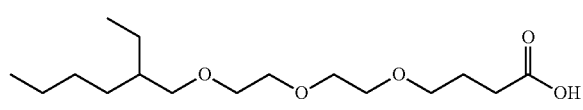

A compound in accordance with an embodiment of the present invention contains various oxa acids having different HLB values. A compound in accordance with an embodiment of the present invention has an HLB value of preferably 3 to 15, more preferably 3 to 9.

In a case where, for instance, a compound in accordance with an embodiment of the present invention has the combination (E) or (J) above, that compound will have a low HLB value within a range of 3 to 5.

In a case where, for instance, $R^1$ in the formula (1) above has 2 or 3 carbon atoms or $R^2$ in the formula (2) above has 2 or 3 carbon atoms, the compound having such $R^1$ or $R^2$ will have a high HLB value within a range of 8 to 9.

A compound in accordance with an embodiment of the present invention, which contains various oxa acids having different hydrophile-lipophile balances as described above, is suitably usable in the polarity control for the dosage form design in the fields of DDS and cosmetics.

The HLB value for the present invention is an HLB value calculated by Davis method. Davis method refers to a method of calculating an HLB value by dividing a molecule into groups (atomic groups) and using HLB group numbers given to various groups and unique to the respective groups. Specifically, the HLB value is calculated on the basis of "The hydrophilic-lipophilic balance (HLB) of the emulsifier" at pages 429 to 431 of "Gas/Liquid and Liquid/Liquid Interfaces. Proceedings of 2nd International Congress Surface Activity, Butterworths, London 1957".

[Method for Producing a Compound in Accordance with an Embodiment of the Present Invention]

A compound in accordance with an embodiment of the present invention can be produced by, for example, the method described below. The method for producing a compound in accordance with an embodiment of the present invention is, however, not limited to the method described below.

First, cyclic lactone and alcohols represented respectively by the formulae (16) and (17) below are subjected to esterification and etherification. Next, the products resulting from the reactions are hydrolyzed to produce compounds (carboxylic acids) which are represented respectively by the formulae (1) and (2) and in which X represents —OH. Then, the carboxy group of each carboxylic acid produced is derivatized through esterification, amidation, or any of other various publicly known functional group interconversions to produce compounds having respective structures represented respectively by the formulae (1) and (2) above.

[Chem. 19]

(16)

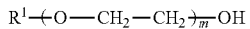

[Chem. 20]

(17)

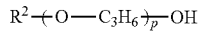

Specifically, an example method for producing a compound having the structure represented by the formula (1) above in accordance with an embodiment of the present invention includes at least (i) reacting cyclic lactone and an alcohol having the structure represented by the formula (16) above with each other and (ii) hydrolyzing the product resulting from the step (i). The example method for producing a compound having the structure represented by the formula (1) above in accordance with an embodiment of the present invention may further include (iii) derivatizing the carboxyl group of the compound (carboxylic acid) which has resulted from the step (ii), which is represented by the formula (1), and in which X represents —OH.

An example method for producing a compound having the structure represented by the formula (2) above in accordance with an embodiment of the present invention includes at least (i) reacting cyclic lactone and an alcohol having the structure represented by the formula (17) above with each other and (ii) hydrolyzing the product resulting from the step (i). The example method for producing a compound having the structure represented by the formula (2) above in accordance with an embodiment of the present invention may further include (iii) derivatizing the carboxyl group of the compound (carboxylic acid) which has resulted from the step (ii), which is represented by the formula (2), and in which X represents —OH.

The cyclic lactone for use in the method for producing compounds represented respectively by the formulae (1) and (2) is, for example, β-propiolactone, γ-butyrolactone, δ-valerolactone, or ε-caprolactone.

A compound in accordance with an embodiment of the present invention can be made usable as a promotor of absorption of a biofunctional molecule such as a physiologically active protein, a peptide, an antibody, a nucleic acid, and a low-molecular-weight pharmaceutical drug by (i) subjecting the compound to the above reactions sufficiently and then (ii) purifying the product as appropriate by publicly known methods such as reduced-pressure distillation, silica gel chromatography, and crystallization. A compound in accordance with an embodiment of the present invention is usable also as a chemical modifier for a pharmaceutical drug carrier such as liposome and polymeric micelle or as a promotor of absorption of the above carrier.

A compound in accordance with an embodiment of the present invention may, needless to say, cover in its scope a compound before the purification or a compound after the purification.

The present invention is not limited to the embodiments, but can be altered by a skilled person in the art within the scope of the claims. The present invention also encompasses, in its technical scope, any embodiment derived by combining technical means disclosed in differing embodiments.

An embodiment of the present invention is configured as below.

[1] A compound, including a structure represented by a formula (1) below:

[Chem. 21]

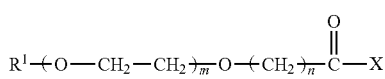

(1)

where $R^1$ represents a linear or branched hydrocarbon group having 1 to 36 carbon atoms, one or more but not all carbon atoms of which hydrocarbon group have each optionally been substituted by an oxygen atom, a nitrogen atom, or a sulfur atom; m represents an integer of 0 to 35; n represents an integer of 2 to 5; and —C(=O)—X represents a functional group capable of chemical reaction, or a formula (2) below:

[Chem. 22]

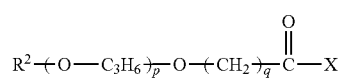

(2)

where $R^2$ represents a linear or branched hydrocarbon group having 1 to 36 carbon atoms, one or more but not all carbon atoms of which hydrocarbon group have each optionally been substituted by an oxygen atom, a nitrogen atom, or a sulfur atom; p represents an integer of 0 to 30; q represents an integer of 2 to 5; and —C(=O)—X represents a functional group capable of chemical reaction.

[2] The compound according to [1], wherein: in the formula (1), $R^1$ represents a linear or branched hydrocarbon group having 2 to 36 carbon atoms, one or more but not all carbon atoms of which hydrocarbon group have each optionally been substituted by an oxygen atom, a nitrogen atom, or a sulfur atom; m represents an integer of 0 to 20; and n represents an integer of 3 or 4, and in the formula (2), $R^2$ represents a linear or branched hydrocarbon group having 2 to 36 carbon atoms, one or more but not all carbon atoms of which hydrocarbon group have each optionally been substituted by an oxygen atom, a nitrogen atom, or a sulfur atom; p represents an integer of 0 to 20; and q represents an integer of 3 or 4.

[3] The compound according to [1] or [2], wherein: in the formula (1), $R^1$ represents a linear or branched hydrocarbon group having 4 to 36 carbon atoms, one or more but not all carbon atoms of which hydrocarbon group have each optionally been substituted by an oxygen atom, a nitrogen atom, or a sulfur atom; m represents an integer of 0 to 20; and n represents an integer of 3 or 4, and in the formula (2), $R^2$ represents a linear or branched hydrocarbon group having 4 to 36 carbon atoms, one or more but not all carbon atoms of which hydrocarbon group have each optionally been substituted by an oxygen atom, a nitrogen atom, or a sulfur atom; p represents an integer of 0 to 20; and q represents an integer of 3 or 4.

[4] The compound according to any one of [1] to [3], wherein: in the formula (1), $R^1$ represents a linear or branched hydrocarbon group having 6 to 36 carbon atoms, one or more but not all carbon atoms of which hydrocarbon group have each optionally been substituted by an oxygen atom, a nitrogen atom, or a sulfur atom; m represents an integer of 0 to 20; and n represents an integer of 3 or 4, and in the formula (2), $R^2$ represents a linear or branched hydrocarbon group having 6 to 36 carbon atoms, one or more but not all carbon atoms of which hydrocarbon group have each optionally been substituted by an oxygen atom, a nitrogen atom, or a sulfur atom; p represents an integer of 0 to 20; and q represents an integer of 3 or 4.

[5] The compound according to any one of [1] to [4], wherein: in the formula (1), $R^1$ represents a linear or branched hydrocarbon group having 8 to 36 carbon atoms, one or more but not all carbon atoms of which hydrocarbon group have each optionally been substituted by an oxygen atom, a nitrogen atom, or a sulfur atom; m represents an integer of 0 to 20; and n represents an integer of 3 or 4, and in the formula (2), $R^2$ represents a linear or branched hydrocarbon group having 8 to 36 carbon atoms, one or more but not all carbon atoms of which hydrocarbon group have each optionally been substituted by an oxygen atom, a nitrogen atom, or a sulfur atom; p represents an integer of 0 to 20; and q represents an integer of 3 or 4.

[6] The compound according to any one of [1] to [5], wherein: in the formula (1), $R^1$ represents a linear or branched hydrocarbon group having 9 to 36 carbon atoms, one or more but not all carbon atoms of which hydrocarbon group have each optionally been substituted by an oxygen atom, a nitrogen atom, or a sulfur atom; m represents an integer of 0 to 20; and n represents an integer of 3 or 4, and in the formula (2), $R^2$ represents a linear or branched hydrocarbon group having 9 to 36 carbon atoms, one or more but not all carbon atoms of which hydrocarbon group have each optionally been substituted by an oxygen atom, a nitrogen atom, or a sulfur atom; p represents an integer of 0 to 20; and q represents an integer of 3 or 4.

[7] The compound according to any one of [1] to [6], wherein: in the formula (1), n represents 3, and in the formula (2), q represents 3.

[8] The compound according to any one of [1] to [7], wherein: in the formula (1), $R^1$ represents a linear hydrocarbon group, and in the formula (2), $R^2$ represents a linear hydrocarbon group.

[9] A compound having a structure represented by one of chemical formulae (3) to (15) below:

[Chem. 23]

(3)

[Chem. 24]

(4)

[Chem. 25]

(5)

[Chem. 26]

(6)

[Chem. 27]

(7)

[Chem. 28]

(8)

[Chem. 29]

(9)

[Chem. 30]

(10)

[Chem. 31]

(11)

[Chem. 32]

(12)

[Chem. 33]

(13)

[Chem. 34]

(14)

[Chem. 35]

(15)

EXAMPLES

The following will specifically describe the present invention with reference to Examples, but the present invention is not limited to the Examples.

Example 1: Production of a Compound Represented by the Formula (3)

Into a 10-liter glass container equipped with a dehydrating tower, (i) 861 g of γ-butyrolactone, (ii) 1320 g of an alcohol represented by the formula (16) above with $R^1$ representing —$CH_2$—$CH_2$—$CH(CH_3)$—$CH_3$ and m representing 1, and (iii) 19 g of p-toluenesulfonic acid were charged. The three ingredients were stirred at 120° C. for 64 hours for reaction. Then, the unreacted portion was removed by distillation at 400 Pa and 150° C. This produced a crude product. Next, 4000 g of water and 112 g of potassium hydroxide were added to the crude product, and the three components were stirred at 80° C. for 2 hours for hydrolysis. Then, hydrochloric acid was added to the mixture until the reaction solution became acidic. The reaction solution was left standing still, and then an organic layer was separated from the reaction solution. This organic layer was washed three times with a 10% by weight aqueous sodium acetate solution. Then, 160 g of a compound represented by the formula (3) was separated as a fraction at 400 Pa and a temperature within a range of 155° C. to 165° C. FIG. 1 shows a $^1$H-NMR chart for the resulting compound, and Table 1 shows its HLB.

Example 2: Production of a Compound Represented by the Formula (4)

Into a 10-liter glass container equipped with a dehydrating tower, (i) 861 g of γ-butyrolactone, (ii) 1341 g of an alcohol represented by the formula (16) above with $R^1$ representing —$CH_2$—$CH_3$ and m representing 2, and (iii) 19 g of p-toluenesulfonic acid were charged. The three ingredients were stirred at 120° C. for 64 hours for reaction. Then, the unreacted portion was removed by distillation at 400 Pa and 150° C. This produced a crude product. Next, 4000 g of water and 112 g of potassium hydroxide were added to the crude product, and the three components were stirred at 80° C. for 2 hours for hydrolysis. Then, hydrochloric acid was added to the mixture until the reaction solution became acidic. The reaction solution was left standing still, and then an organic layer was separated from the reaction solution. This organic layer was washed three times with a 10% by weight aqueous sodium acetate solution. Then, 140 g of a compound represented by the formula (4) was separated as a fraction at 400 Pa and a temperature within a range of 155° C. to 165° C. Table 1 shows the HLB of the resulting compound.

Example 3: Production of a Compound Represented by the Formula (5)

Into a 10-liter glass container equipped with a dehydrating tower, (i) 861 g of γ-butyrolactone, (ii) 1443 g of an alcohol represented by the formula (16) above with $R^1$ representing —$(CH_2)_8$—$CH_3$ and m representing 0, and (iii) 19 g of p-toluenesulfonic acid were charged. The three ingredients were stirred at 120° C. for 64 hours for reaction. Then, the unreacted portion was removed by distillation at 400 Pa and 150° C. This produced a crude product. Next, 4000 g of water and 112 g of potassium hydroxide were added to the crude product, and the three components were stirred at 80° C. for 2 hours for hydrolysis. Then, hydrochloric acid was added to the mixture until the reaction solution became acidic. The reaction solution was left standing still, and then an organic layer was separated from the reaction solution. This organic layer was washed three times with a 10% by weight aqueous sodium acetate solution. Then, 184 g of a compound represented by the formula (5) was separated as a fraction at 400 Pa and a temperature within a range of 165° C. to 175° C. Table 1 shows the HLB of the resulting compound.

Example 4: Production of a Compound Represented by the Formula (6)

Figure 2:
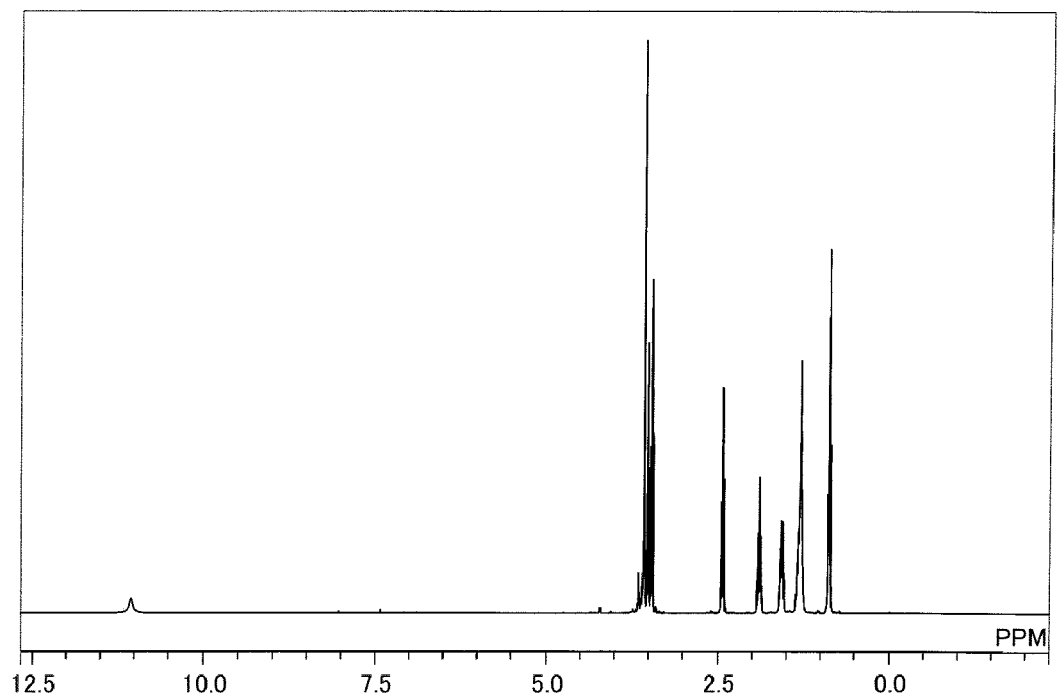
FIG. 2 is a $^1$H-NMR chart for a compound produced in Example 4 of the present invention.

Into a 10-liter glass container equipped with a dehydrating tower, (i) 861 g of γ-butyrolactone, (ii) 1462 g of an alcohol represented by the formula (16) above with $R^1$ representing —$(CH_2)_5$—$CH_3$ and m representing 1, and (iii) 19 g of p-toluenesulfonic acid were charged. The three ingredients were stirred at 120° C. for 64 hours for reaction. Then, the unreacted portion was removed by distillation at 400 Pa and 150° C. This produced a crude product. Next, 4000 g of water and 112 g of potassium hydroxide were added to the crude product, and the three components were stirred at 80° C. for 2 hours for hydrolysis. Then, hydrochloric acid was added to the mixture until the reaction solution became acidic. The reaction solution was left standing still, and then an organic layer was separated from the reaction solution. This organic layer was washed three times with a 10% by weight aqueous sodium acetate solution. Then, 163 g of a compound represented by the formula (6) was separated as a fraction at 400 Pa and a temperature within a range of 165° C. to 175° C. FIG. 2 shows a $^1$H-NMR chart for the resulting compound, and Table 1 shows its HLB.

Example 5: Production of a Compound Represented by the Formula (7)

Into a 10-liter glass container equipped with a dehydrating tower, (i) 861 g of γ-butyrolactone, (ii) 1482 g of an alcohol represented by the formula (16) above with $R^1$ representing —$CH(CH_3)$—$CH_3$ and m representing 2, and (iii) 19 g of p-toluenesulfonic acid were charged. The three ingredients were stirred at 120° C. for 64 hours for reaction. Then, the unreacted portion was removed by distillation at 400 Pa and 150° C. This produced a crude product. Next, 4000 g of water and 112 g of potassium hydroxide were added to the crude product, and the three components were stirred at 80° C. for 2 hours for hydrolysis. Then, hydrochloric acid was added to the mixture until the reaction solution became acidic. The reaction solution was left standing still, and then an organic layer was separated from the reaction solution. This organic layer was washed three times with a 10% by weight aqueous sodium acetate solution. Then, 153 g of a compound represented by the formula (7) was separated as a fraction at 400 Pa and a temperature within a range of 165° C. to 175° C. Table 1 shows the HLB of the resulting compound.

Example 6: Production of a Compound Represented by the Formula (8)

Into a 10-liter glass container equipped with a dehydrating tower, (i) 861 g of γ-butyrolactone, (ii) 1583 g of an alcohol represented by the formula (16) above with $R^1$ representing —$(CH_2)_9$—$CH_3$ and m representing 0, and (iii) 19 g of p-toluenesulfonic acid were charged. The three ingredients were stirred at 120° C. for 64 hours for reaction. Then, the unreacted portion was removed by distillation at 400 Pa and 150° C. This produced a crude product. Next, 4000 g of water and 112 g of potassium hydroxide were added to the crude product, and the three components were stirred at 80° C. for 2 hours for hydrolysis. Then, hydrochloric acid was added to the mixture until the reaction solution became acidic. The reaction solution was left standing still, and then an organic layer was separated from the reaction solution. This organic layer was washed three times with a 10% by weight aqueous sodium acetate solution. Then, 208 g of a compound represented by the formula (8) was separated as a fraction at 400 Pa and a temperature within a range of 170° C. to 180° C. Table 1 shows the HLB of the resulting compound.

Example 7: Production of a Compound Represented by the Formula (9)

Into a 10-liter glass container equipped with a dehydrating tower, (i) 861 g of γ-butyrolactone, (ii) 1622 g of an alcohol represented by the formula (16) above with $R^1$ representing —$(CH_2)_3$—$CH_3$ and m representing 2, and (iii) 19 g of p-toluenesulfonic acid were charged. The three ingredients were stirred at 120° C. for 64 hours for reaction. Then, the unreacted portion was removed by distillation at 400 Pa and 150° C. This produced a crude product. Next, 4000 g of water and 112 g of potassium hydroxide were added to the crude product, and the three components were stirred at 80° C. for 2 hours for hydrolysis. Then, hydrochloric acid was added to the mixture until the reaction solution became acidic. The reaction solution was left standing still, and then an organic layer was separated from the reaction solution. This organic layer was washed three times with a 10% by weight aqueous sodium acetate solution. Then, 186 g of a compound represented by the formula (9) was separated as a fraction at 400 Pa and a temperature within a range of 165° C. to 175° C. Table 1 shows the HLB of the resulting compound.

Example 8: Production of a Compound Represented by the Formula (10)

Into a 10-liter glass container equipped with a dehydrating tower, (i) 861 g of γ-butyrolactone, (ii) 1622 g of an alcohol represented by the formula (16) above with R¹ representing —CH₂—CH(CH₃)—CH₃ and m representing 2, and (iii) 19 g of p-toluenesulfonic acid were charged. The three ingredients were stirred at 120° C. for 64 hours for reaction. Then, the unreacted portion was removed by distillation at 400 Pa and 150° C. This produced a crude product. Next, 4000 g of water and 112 g of potassium hydroxide were added to the crude product, and the three components were stirred at 80° C. for 2 hours for hydrolysis. Then, hydrochloric acid was added to the mixture until the reaction solution became acidic. The reaction solution was left standing still, and then an organic layer was separated from the reaction solution. This organic layer was washed three times with a 10% by weight aqueous sodium acetate solution. Then, 149 g of a compound represented by the formula (10) was separated as a fraction at 400 Pa and a temperature within a range of 165° C. to 175° C. Table 1 shows the HLB of the resulting compound.

Example 9: Production of a Compound Represented by the Formula (11)

Figure 3:
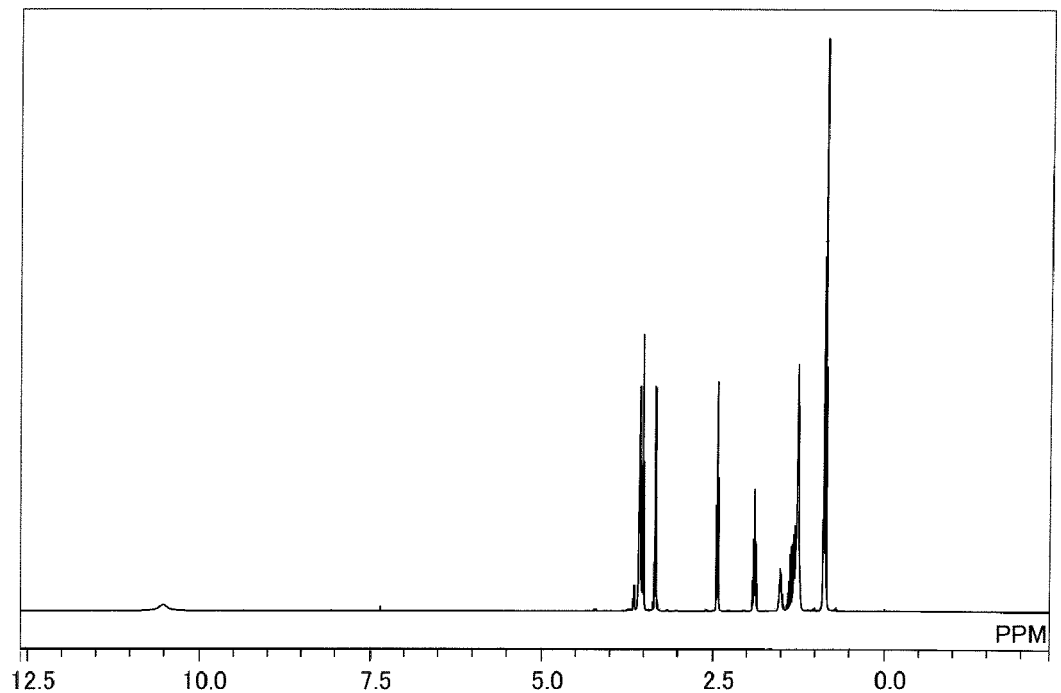
FIG. 3 is a $^1$H-NMR chart for a compound produced in Example 9 of the present invention.

Into a 10-liter glass container equipped with a dehydrating tower, (i) 861 g of γ-butyrolactone, (ii) 1742 g of an alcohol represented by the formula (16) above with R¹ representing —CH₂—CH(CH₂—CH₃)—(CH₂)₃—CH₃ and m representing 1, and (iii) 19 g of p-toluenesulfonic acid were charged. The three ingredients were stirred at 120° C. for 64 hours for reaction. Then, the unreacted portion was removed by distillation at 400 Pa and 150° C. This produced a crude product. Next, 4000 g of water and 112 g of potassium hydroxide were added to the crude product, and the three components were stirred at 80° C. for 2 hours for hydrolysis. Then, hydrochloric acid was added to the mixture until the reaction solution became acidic. The reaction solution was left standing still, and then an organic layer was separated from the reaction solution. This organic layer was washed three times with a 10% by weight aqueous sodium acetate solution. Then, 211 g of a compound represented by the formula (11) was separated as a fraction at 400 Pa and a temperature within a range of 180° C. to 190° C. FIG. 3 shows a ¹H-NMR chart for the resulting compound, and Table 1 shows its HLB.

Example 10: Production of a Compound Represented by the Formula (12)

Into a 10-liter glass container equipped with a dehydrating tower, (i) 861 g of γ-butyrolactone, (ii) 1863 g of an alcohol represented by the formula (16) above with R¹ representing —(CH₂)₁₁—CH₃ and m representing 0, and (iii) g of p-toluenesulfonic acid were charged. The three ingredients were stirred at 120° C. for 64 hours for reaction. Then, the unreacted portion was removed by distillation at 400 Pa and 150° C. This produced a crude product. Next, 4000 g of water and 112 g of potassium hydroxide were added to the crude product, and the three components were stirred at 80° C. for 2 hours for hydrolysis. Then, hydrochloric acid was added to the mixture until the reaction solution became acidic. The reaction solution was left standing still, and then an organic layer was separated from the reaction solution. This organic layer was washed three times with a 10% by weight aqueous sodium acetate solution. Then, 232 g of a compound represented by the formula (12) was separated as a fraction at 400 Pa and a temperature within a range of 195° C. to 205° C. Table 1 shows the HLB of the resulting compound.

Example 11: Production of a Compound Represented by the Formula (13)

Figure 4:
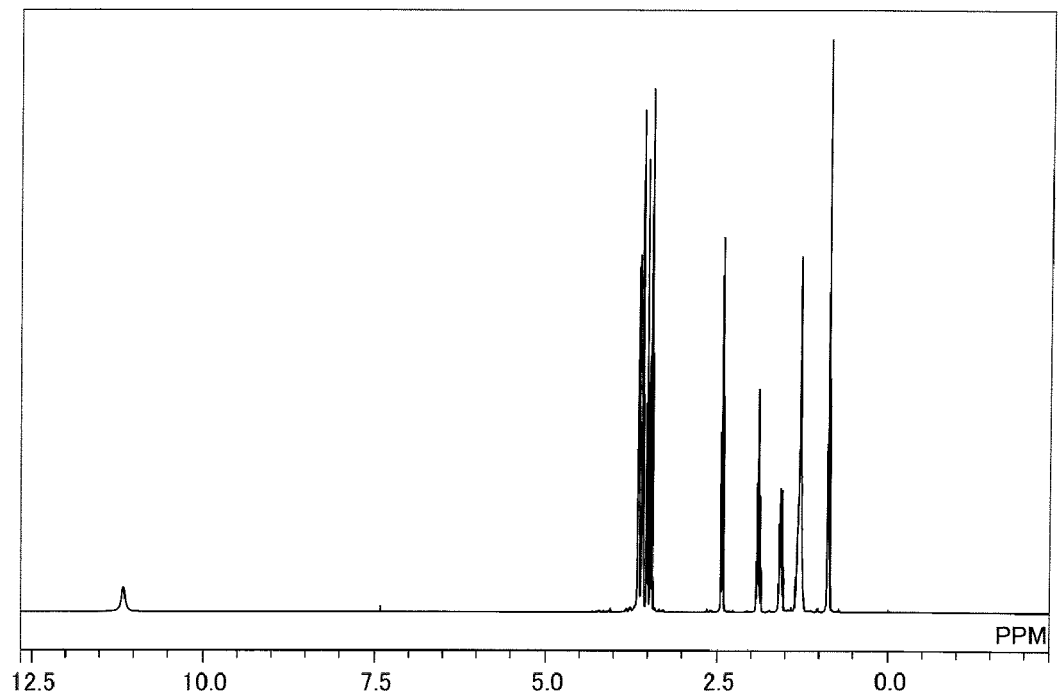
FIG. 4 is a $^1$H-NMR chart for a compound produced in Example 11 of the present invention.

Into a 10-liter glass container equipped with a dehydrating tower, (i) 861 g of γ-butyrolactone, (ii) 1903 g of an alcohol represented by the formula (16) above with R¹ representing —(CH₂)₅—CH₃ and m representing 2, and (iii) 19 g of p-toluenesulfonic acid were charged. The three ingredients were stirred at 120° C. for 64 hours for reaction. Then, the unreacted portion was removed by distillation at 400 Pa and 150° C. This produced a crude product. Next, 4000 g of water and 112 g of potassium hydroxide were added to the crude product, and the three components were stirred at 80° C. for 2 hours for hydrolysis. Then, hydrochloric acid was added to the mixture until the reaction solution became acidic. The reaction solution was left standing still, and then an organic layer was separated from the reaction solution. This organic layer was washed three times with a 10% by weight aqueous sodium acetate solution. Then, 221 g of a compound represented by the formula (13) was separated as a fraction at 400 Pa and a temperature within a range of 190° C. to 200° C. FIG. 4 shows a ¹H-NMR chart for the resulting compound, and Table 1 shows its HLB.

Example 12: Production of a Compound Represented by the Formula (14)

Figure 5:
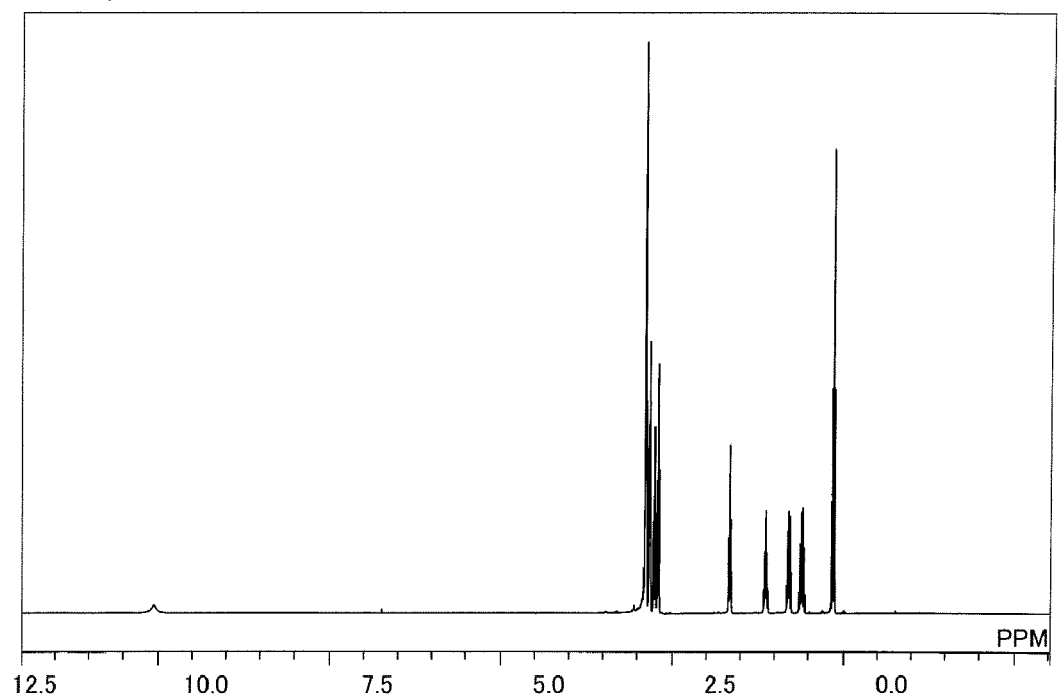
FIG. 5 is a $^1$H-NMR chart for a compound produced in Example 12 of the present invention.

Into a 10-liter glass container equipped with a dehydrating tower, (i) 861 g of γ-butyrolactone, (ii) 2063 g of an alcohol represented by the formula (16) above with R¹ representing —(CH₂)₃—CH₃ and m representing 3, and (iii) 19 g of p-toluenesulfonic acid were charged. The three ingredients were stirred at 120° C. for 64 hours for reaction. Then, the unreacted portion was removed by distillation at 400 Pa and 150° C. This produced a crude product. Next, 4000 g of water and 112 g of potassium hydroxide were added to the crude product, and the three components were stirred at 80° C. for 2 hours for hydrolysis. Then, hydrochloric acid was added to the mixture until the reaction solution became acidic. The reaction solution was left standing still, and then an organic layer was separated from the reaction solution. This organic layer was washed three times with a 10% by weight aqueous sodium acetate solution. Then, 175 g of a compound represented by the formula (14) was separated as a fraction at 400 Pa and a temperature within a range of 190° C. to 200° C. FIG. 5 shows a ¹H-NMR chart for the resulting compound, and Table 1 shows its HLB.

Example 13: Production of a Compound Represented by the Formula (15)

Figure 6:
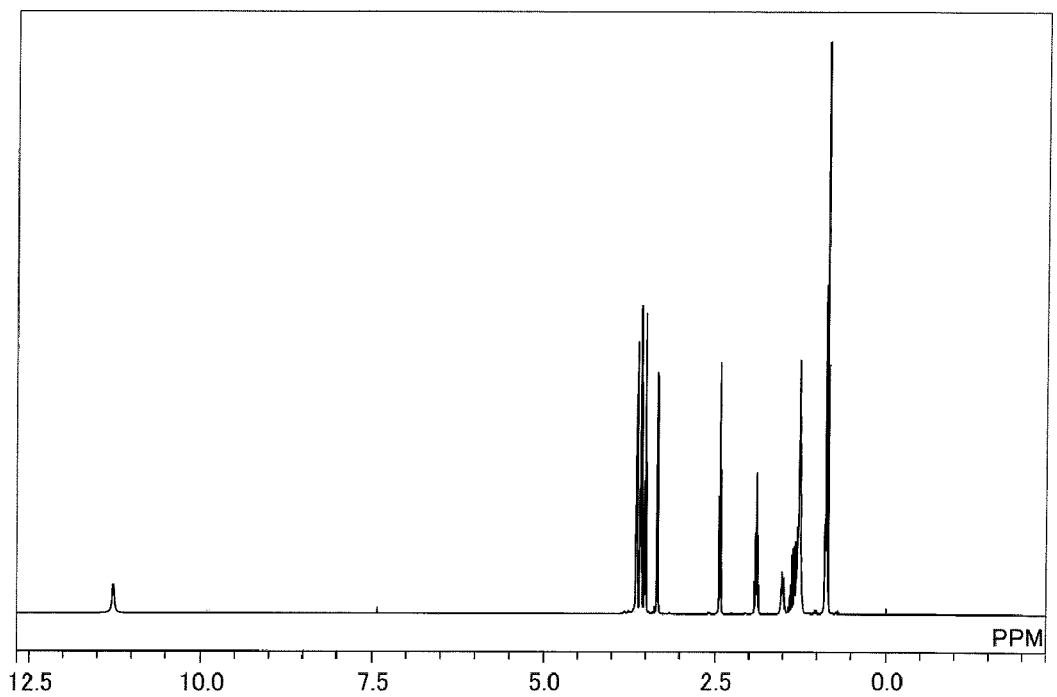
FIG. 6 is a $^1$H-NMR chart for a compound produced in Example 13 of the present invention.

Into a 10-liter glass container equipped with a dehydrating tower, (i) 861 g of γ-butyrolactone, (ii) 2183 g of an alcohol represented by the formula (16) above with R¹ representing —CH₂—CH(CH₂—CH₃)—(CH₂)₃—CH₃ and m representing 2, and (iii) 19 g of p-toluenesulfonic acid were charged. The three ingredients were stirred at 120° C. for 64 hours for reaction. Then, the unreacted portion was removed by distillation at 400 Pa and 150° C. This produced a crude product. Next, 4000 g of water and 112 g of potassium hydroxide were added to the crude product, and the three components were stirred at 80° C. for 2 hours for hydrolysis. Then, hydrochloric acid was added to the mixture until the reaction solution became acidic. The reaction solution was left standing still, and then an organic layer was separated from the reaction solution. This organic layer was washed three times with a 10% by weight aqueous sodium acetate solution. Then, 305 g of a compound represented by the formula (15) was separated as a fraction at 400 Pa and a temperature within a range of 200° C. to 215° C. FIG. 6 shows a ¹H-NMR chart for the resulting compound, and Table 1 shows its HLB.

TABLE 1
| EX | STRUCTURE | HLB |
|---|---|---|
| 1 | 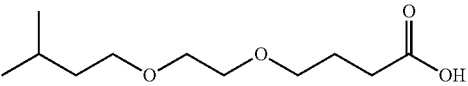 | 6.95 |
| 2 | 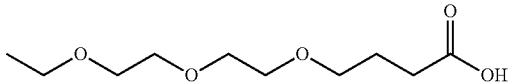 | 8.725 |
| 3 | 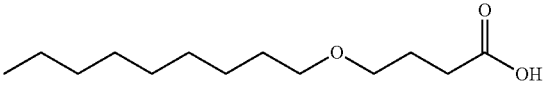 [SMILES: CCCCCCCCCOCCCC(=O)O] | 4.7 |
| 4 | 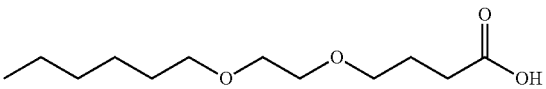 [SMILES: CCCCCCOCCOCCCC(=O)O] | 6.475 |
| 5 | 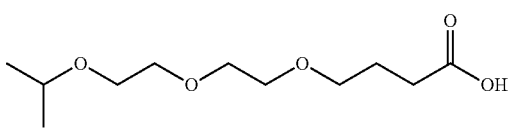 [SMILES: CC(C)OCCOCCOCCCC(=O)O] | 8.25 |
| 6 | 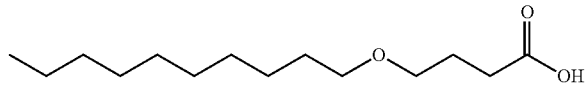 [SMILES: CCCCCCCCCCOCCCC(=O)O] | 4.225 |
| 7 | 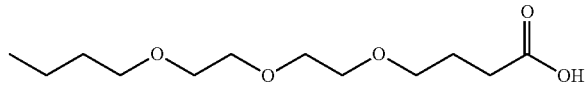 [SMILES: CCCCOCCOCCOCCCC(=O)O] | 7.775 |
| 8 | 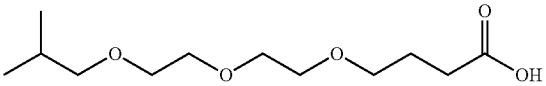 [SMILES: CC(C)COCCOCCOCCCC(=O)O] | 7.775 |
| 9 | 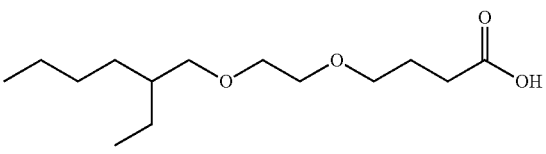 [SMILES: CCCCC(CC)COCCOCCCC(=O)O] | 5.525 |
| 10 | 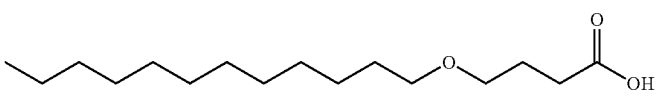 [SMILES: CCCCCCCCCCCCOCCCC(=O)O] | 3.275 |
| 11 | 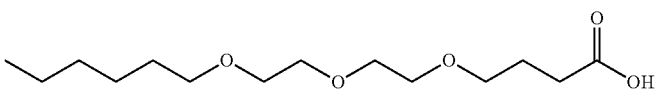 [SMILES: CCCCCCOCCOCCOCCCC(=O)O] | 6.825 |
| 12 | 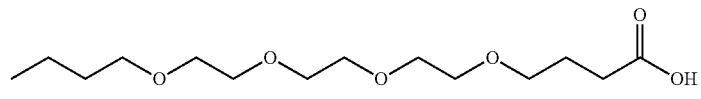 [SMILES: CCCCOCCOCCOCCOCCCC(=O)O] | 8.125 |
| 13 | 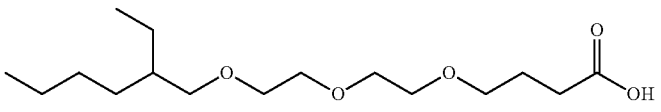 [SMILES: CCCCC(CC)COCCOCCOCCCC(=O)O] | 5.875 |

INDUSTRIAL APPLICABILITY

A compound in accordance with an embodiment of the present invention is usable in such applications as an application as an absorption promotor in the fields of DDSs and cosmetics or an application for producing a prodrug of a pharmacologically active substance, and is particularly useful.

The invention claimed is:

1. A compound corresponding in structure to one of the following:

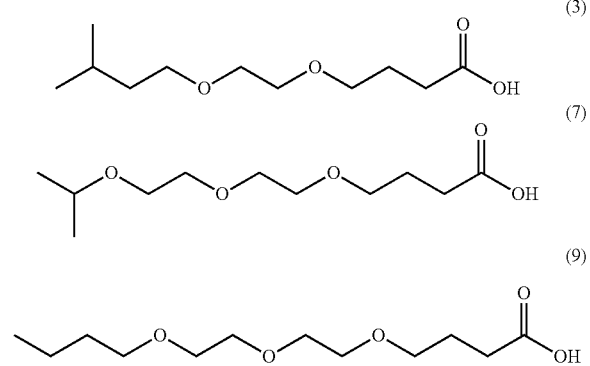

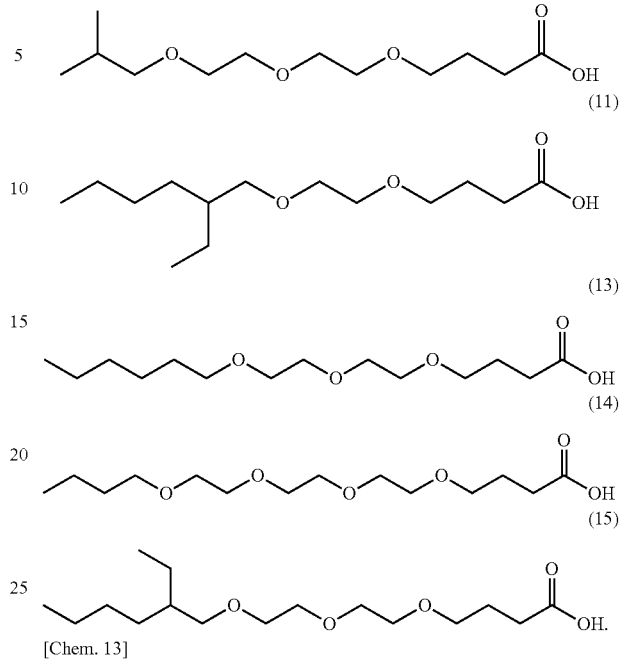

[Chem. 13]

* * * * *